United States Patent [19]

Masaki et al.

[11] Patent Number: 5,231,166
[45] Date of Patent: Jul. 27, 1993

[54] ENDOTHELIN

[75] Inventors: Tomoh Masaki; Masashi Yanagisawa; Akihiro Inoue, all of Ibaraki, Japan

[73] Assignee: Takeda Chemical Industries, Ltd., Osaka, Japan

[21] Appl. No.: 422,132

[22] Filed: Oct. 16, 1989

[30] Foreign Application Priority Data

Oct. 25, 1988 [JP] Japan ................................ 63-267149
May 29, 1989 [JP] Japan ................................ 1-132705

[51] Int. Cl.$^5$ ................................................ C07K 7/00
[52] U.S. Cl. ...................................... 530/324; 530/326
[58] Field of Search ............................... 530/324, 326

[56] References Cited

U.S. PATENT DOCUMENTS 4,981,950 1/1991 Masaki et al. ...................... 530/326

OTHER PUBLICATIONS

Saida et al. *J. of Biol Chem* 264(25) 14613-14616 (1989).
Inoue et al. *Proc Natl Acad Sci USA* 86:2863-2867 (1989).
Itoh et al. *Nucl Acids Res* 17(13):5389 (1989).
Bloch et al. *J. of Biol Chem* 264(18):10851-10857 (1989).
Kimura et al. *Nucl Acids Res* 17(8):3290 (1989).
Tatemoto, *Proc Natl Acad Sci USA* 79:5485-89 (1982).
Shinmi et al. *Biochem Biophys Res Comm* 162(1):340-346 (1989).
Minth et al., *Proc Natl Acad Sci USA* 81:4577-4581 (1984).
Inoue et al. *J. of Biol Chem* 264(25):14954-59 (1989).
Sawaamura et al. *Biochem Biophys Res Comm* 162(3):1287-94 (1989).
M. Yanagisawa, et al., Nature, 332:441-5, Mar. 31, 1988.
Y. Itoh, et al., FEBS Letters, 321:(2):440-4, Apr. 1988.
M. Yanagisawa, et al., Abstract C-5, 77th Japan Pharmacological Meeting.
I. Kifor, et al., Circulation Research vol. 60, No. 3, 422-28 1987.
K. Hickey, et al., Am. J.Physiol. 248 (Cell Physiol. 17), C550-56 (1985).
R. O'Brien, et al., Journal of Cellular Physiology 132:263-270 (1987).
M. Gillespie, et al., The Journal of Pharmacology and Experimental Therapeutics, vol. 236, No. 2, 339-43.

*Primary Examiner*—Robert J. Hill, Jr.
*Assistant Examiner*—Shelly J. Guest
*Attorney, Agent, or Firm*—David G. Conlin; George W. Neuner

[57] ABSTRACT

Endothelin-2 and a big type of endothelin-2 proteins are described. The proteins contain the amino acid sequence: Cys Ser Cys Ser Ser Trp Leu Asp Lys Glu Cys Val Tyr Phe Cys His Leu Asp Ile Ile Trp.

2 Claims, 3 Drawing Sheets

FIGURE 2

Human Endothelin A-II (the present invention)

CATGCCCAAGGCACCACCCTTCGGCTTCGCCGTTGCTCCTGAGCTCCTGGCTCCTGACAAGGAGTGGTCGTCTACTTCTGCCACTTGGACATCATCTGGGTGAACACTCCTGA
HisAlaGlnGlyThrHisLeuArgLeuArgArgCysSerCysSerSerTrpLeuAspIleIleTrpValAsnThrProGlu

Human Endothelin A (prior application)

AGTCCACCCTGGGGCTCCGCCGGTCCAAGCGGTGCTCCTGCTCGTCCCTGATGGATAAAGAGTGTGTCTACTTCTGCCACCTTGGACATCATTGGGTCAACACTCCCGA
SerProProTrpArgLeuArgArgSerArgCysSerCysSerLeuMetAspLysGluCysValTyrPheCysHisLeuAspIleIleTrpValAsnThrProGlu

Human endothelin C DNA (the present invention)

GAGGGGGCCCTGAGCACCACCAGGCGGTGCACGTGCTTCACCTACAAGGACAAGGAGTGTGTCTACTATGCCACCTGGACATCATTTGGATCAACACTCCCGA
ArgGlyProGluHisHisArgArgArgCysThrCysPheThrThrLysAspLysGluCysValTyrTyrCysHisLeuAspIleIleTrpIleAsnThrProGlu

Endothelin C (rat endothelin) (prior application)

CACCGACCTCGGCGCTGCAGTGCTTCACTTATAAGGACAAGGAGTGTGTCTACTGCCACCTGGACATCATCTGATCAACACTCCTGA
HisArgProArgArgCysThrCysPheThrThrLysAspLysGluCysValTyrTyrCysHisLeuAspIleIleTrpIleAsnThrProGlu

FIGURE 3

Human Endothelin A-II (the present invention)

Cys Ser Cys Ser Ser Trp Leu Asp Lys Glu Cys Val Tyr Phe Cys His Leu Asp Ile Ile Trp

Endothelin A

Cys Ser Cys Ser Ser Leu Met Asp Lys Glu Cys Val Tyr Phe Cys His Leu Asp Ile Ile Trp

Endothelin B

Cys Ser Cys Asn Ser Trp Leu Asp Lys Glu Cys Val Tyr Phe Cys His Leu Asp Ile Ile Trp

Endothelin C

Cys Thr Cys Phe Thr Thr Lys Asp Lys Glu Cys Val Tyr Tyr Cys His Leu Asp Ile Ile Trp

ENDOTHELIN

BACKGROUND OF THE INVENTION

The present invention relates to a DNA sequence containing a DNA segment coding for a human vasoconstrictive peptide, namely endothelin-2, a precursor protein (or a precursor polypeptide) and a mature protein (or a mature polypeptide) of endothelin-2 and a method for preparing the precursor protein and the mature protein (endothelin-2), and further to a DNA sequence containing a DNA segment coding for human endothelin-3, a precursor protein of human endothelin-3 and a method for preparing endothelin-3.

In this specification, the term "precursor protein" is preferably used to describe a protein which includes an amino acid sequence of a mature peptide and has a portion or all of an amino acid sequence coded with a DNA segment of the peptide at the N-terminus, the C-terminus or both termini thereof.

There have been reports of endothelium-dependent vasoconstrictor reactions to various mechanical and chemical stimuli as well as endothelium-dependent vasodilative reactions. For example, it is known that vasoconstriction can be induced by mechanical loads such as vascular stretch and increased vascular inner pressure, or can be chemically induced by such agents as thrombin. Further, vasoconstriction can be induced by conditions of anoxia. Noradrenaline-induced vasoconstriction can be enhanced by use of neuropeptide Y [K. Takemoto, *Proc. Natl. Acad. Sci. U.S.A.* 79, 5485 (1982); C. Minth et al., *ibid.* 81, 4577 (1984)]. Endothelial cell-derived coronary vascular constrictor factors (each having molecular weights of 8,500 and 3,000) are described in K. A. Hickey et al., *Am. J. Physiol.* 248, C550(1985); and in R. F. O'Brien, *J. Cell Physiol.* 132, 263 (1987). However, their structures are unknown. An endothelial cell-derived peptide-like substance is also described in M. N. Gillespie et al., *J. Pharmac. Exp. Ther.* 236, 339 (1985). However, the structure of that substance is also unknown.

Vasopressin is known as a peptide having a vasoconstrictor activity, and the amino acid sequence thereof was determined. There have been no reports, however, that vasopressin was obtained from mammalian or bird vascular endothelial cells. Although there is a report that an angiotensin having a vasoconstrictor activity was obtained from the endothelial cells of bovine aortas [I. Kifor and V. J. Dzav, *Circ. Res.* 60, 422 (1987)], the angiotensin is a peptide having a molecular weight of only about 1,000.

Some of the present inventors have previously succeeded in isolating porcine endothelin as a peptide having a similar vasoconstrictor activity from the endothelial cells of porcine aortas (Japanese Unexamined Patent Publication No. 206997/1989). Some of the present inventors have also succeeded in isolating human endothelin and cloning porcine endothelin cDNA and human endothelin cDNA (Japanese Patent Application Nos. 275613/1987, 313155/1987, 148158/1988 and 274454/1988). The mature polypeptides of the porcine endothelin and the human endothelin have the same amino acid sequence, and are referred to as endothelin-1.

Further, the present inventors have filed patent applications with respect to the isolation of rat endothelin and the cloning of its cDNA (Japanese Patent Application Nos. 174935/1988 and 188083/1988), and this rat endothelin is referred to as endothelin-3.

Furthermore, the present inventors have also filed a patent application with respect to the isolation of mouse endothelin and the cloning of its cDNA (Japanese Patent Application No. 223389/1988), and this mouse endothelin is referred to as endothelin B.

The amino acid sequences of the endothelin-1, endothelin B and endothelin-3 are shown in FIG. 3 in comparison to one another.

Endothelin is a general term for peptides having a molecular weight of 2500±300 and having 21 amino acid residues, including four cysteine groups located at the 1st, 3rd, 11th and 15th residues from the N-terminus of the amino acid sequence, which form two sets of disulfide bonds. One of the combinations of the disulfide bonds may be 1-15 and 3-11 cysteine groups, and the other may be 1-11 and 3-15. The former is higher in ratio of formation and in activity than the latter.

These above-described endothelins have been called variously, and in the present invention, newly unified names for the endothelins are employed in the present invention. They are shown as compared with the previous names as follows:

| Newly unified names | Previous names |
|---|---|
| endothelin-1 | endothelin A |
| | human endothelin |
| | porcine endothelin |
| | endothelin α |
| endothelin-B | mouse endothelin |
| | endothelin B |
| | endothelin β |
| endothelin-3 | endothelin C |
| | endothelin γ |
| | rat endothelin |

As described above, homologous endothelin peptides have been discovered from various animals. However, no novel homologous genes have been discovered from the same animal species. It is therefore a current subject that novel homologous endothelin is further screened, and the struc .re and activity of the endothelin is studied, thereby examining its usefulness, and that the novel peptide is cloned by gene recombination to pioneer mass production thereof.

SUMMARY OF THE INVENTION

The present inventors have variously studied, considering that important contributions will be made to future studies and medical treatments, if a novel homologous gene having the vasoconstrictor activity described above can be collected and further prepared by gene recombination. As a result, the following information has been obtained, thus arriving at the present invention.

Namely, the present inventors have succeeded in cloning DNA coding for endothelin having an amino acid sequence different from that of the above endothelin-1[human endothelin (endothelin A)] from a human genomic DNA library by using as a probe the synthesized DNA segment coding for a part of the human endothelin described in the patent applications previously filed. The present inventors have also succeeded in pioneering the mass production of the new endothelin by gene recombination. The present inventors have named this human endothelin having the novel amino acid sequence "endothelin-2" (first named "human endothelin A-II").

In the cloning described above, the present inventors have further discovered a new human eldothelin DNA which is the same as the above endothelin-3[rat endothelin (endothelin C)] in amino acid sequence of the mature protein, but different therefrom in nucleotide sequence coding for the mature protein and in precursor amino acid sequence. The present inventors have named this DNA "human endothelin-3 DNA", and the precursor "human endothelin-3 precursor protein".

In accordance with the present invention, there are provided (1) a DNA sequence containing a DNA segment coding for endothelin-2, (2) a precursor protein and a mature peptide of endothelin-2, (3) a transformant carrying a DNA sequence containing a DNA segment coding for endothelin-2 and (4) a method for preparing mature endothelin-2 which comprises culturing the transformant described in (3), producing and accumulating a protein in a culture medium, and collecting the protein thus obtained. There are further provided (5) a DNA sequence containing a DNA segment coding for human endothelin-3, (6) a human endothelin-3 precursor protein, (7) a transformant carrying a DNA sequence containing a DNA segment coding for human endothelin-3 and (8) a method for preparing mature endothelin-3 which comprises culturing the transformant described in (7), producing and accumulating a protein in a culture medium, and collecting the protein thus obtained.

BRIEF DESCRIPTION OF THE DRAWINGS

FIG. 2 shows a nucleotide sequence of the endothelin-2 precursor or mature peptide DNA segment, a nucleotide sequence of the human endothelin-3 DNA segment, nucleotide sequences of endothelin-1 and rat endothelin-3 as comparative examples, and their amino acid sequences presumed therefrom; and FIG. 3 shows an amino acid sequence of the human endothelin-2 mature peptide presumed from the nucleotide sequence shown in FIG. 2, and amino acid sequences of endothelin-1, endothelin B and endothelin-3.

DESCRIPTION OF THE PREFERRED EMBODIMENTS

Figure 1:
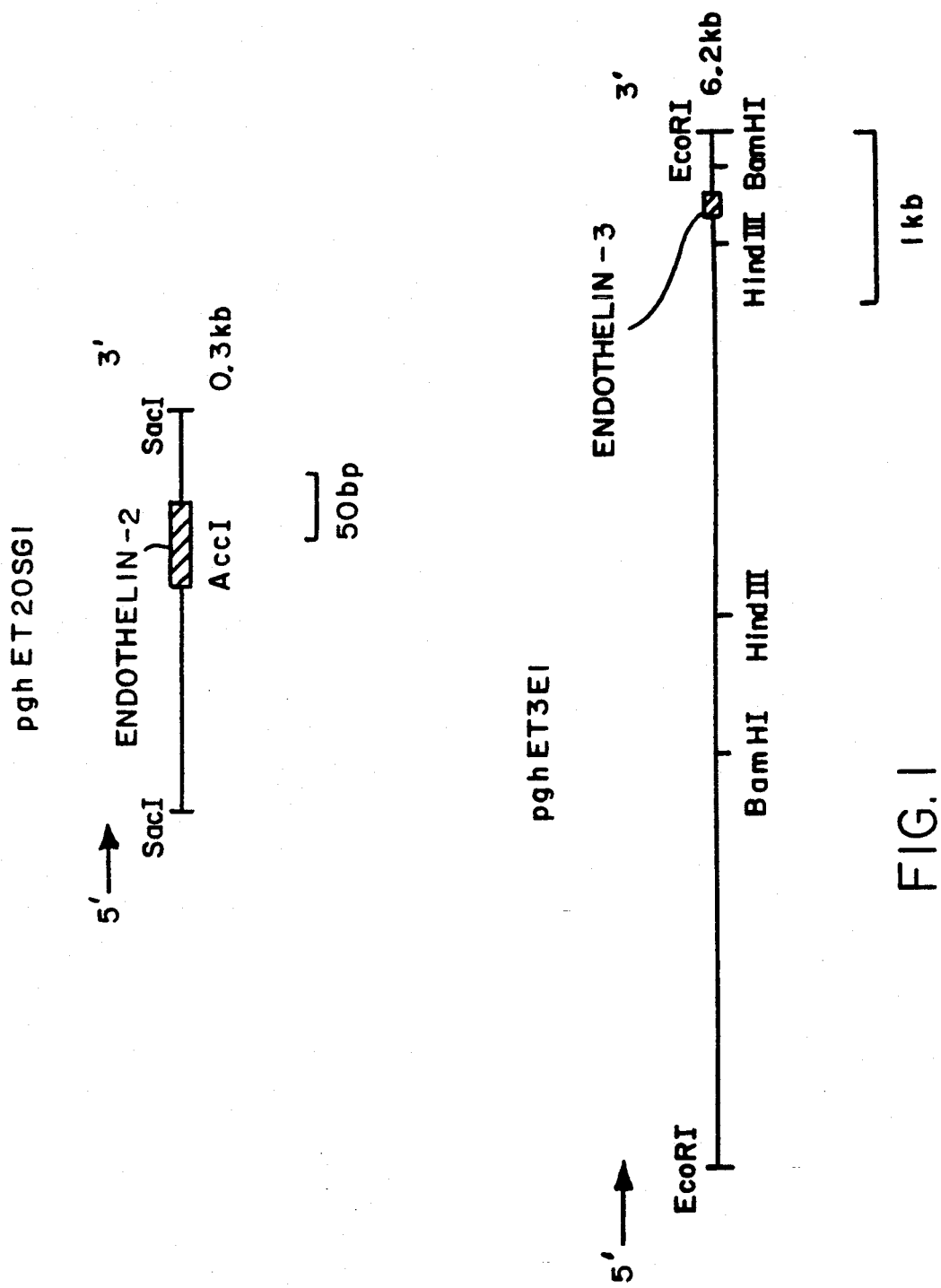
FIG. 1 shows simplified restriction enzyme maps of a DNA sequence containing an endothelin-2 precursor or mature peptide DNA segment and of a DNA sequence containing a human endothelin-3 DNA segment.

Endothelin-2 precursor of the present invention comprises the following amino acid sequence [formula (2)].

(2)
| 1 | 2 | 3 | 4 | 5 | 6 | 7 | 8 | 9 | 10 |
|---|---|---|---|---|---|---|---|---|---|
| His | Ala | Gln | Gly | Thr | His | Leu | Arg | Leu | Arg |

| 11 | 12 | 13 | 14 | 15 | 16 | 17 | 18 | 19 | 20 |
|---|---|---|---|---|---|---|---|---|---|
| Arg | Cys | Ser | Cys | Ser | Ser | Trp | Leu | Asp | Lys |

| 21 | 22 | 23 | 24 | 25 | 26 | 27 | 28 | 29 | 30 |
|---|---|---|---|---|---|---|---|---|---|
| Glu | Cys | Val | Tyr | Phe | Cys | His | Leu | Asp | Ile |

| 31 | 32 | 33 | 34 | 35 | 36 | 37 |
|---|---|---|---|---|---|---|
| Ile | Trp | Val | Asn | Thr | Pro | Glu |

Mature endothelin-2 of the present invention corresponding to human-derived mature endothelin (endothelin-1) and consisting of 21 amino acid residues has an amino acid sequence represented by the following formula (2') which corresponds to No. 12 to 32 of the formula (2):

(2')
| 1 | 2 | 3 | 4 | 5 | 6 | 7 | 8 | 9 | 10 | 11 | 12 | 13 | 14 |
|---|---|---|---|---|---|---|---|---|---|---|---|---|---|
| Cys | Ser | Cys | Ser | Ser | Trp | Leu | Asp | Lys | Glu | Cys | Val | Tyr | Phe |

| 15 | 16 | 17 | 18 | 19 | 20 | 21 |
|---|---|---|---|---|---|---|
| Cys | His | Leu | Asp | Ile | Ile | Trp | (Mol. wt. = 2547)

The numbers of the amino acid residues in the above formula are given in order starting from the first Cys with respect to the amino acid sequence of mature endothelin-2, and different from the numbers given to a endothelin-2 precursor in the formula (2).

Endothelin-2 is different from endothelin-1 in the amino acid residues underlined in the above formula and has the amino acid residues of $$\underset{\text{Trp—Leu}}{\overset{6\quad 7}{}} \text{ in place of } \underset{\text{Leu—Met}}{\overset{6\quad 7}{}}$$

in endothelin-1.

A DNA sequence of the present invention coding for endothelin-2 contains a nucleotide sequence represented by the following formula (1) or a portion thereof:

Endothelin-2
(1)
CAT GCC CAA GGC ACC CAC CTT CGG CTT CGC
↓ 34
CGT TGC TCC TGC AGC TCC TGG CTC GAC AAG
GAG TGC GTC TAC TTC TGC CAC TTG GAC ATC
96 ↓
ATC TGG GTG AAC ACT CCT GA This DNA sequence is widely different from those of the known endothelin-1, endothelin B and endothelin-3 as shown in FIG. 2.

Further, a DNA sequence of the present invention coding for human endothelin-3 has a nucleotide sequence represented by the following formula (3) or a portion thereof:

Human endothelin-3 DNA
(3)
GAG GGG GCC CCT GAG CAC CAC CGA TCC AGG
↓ 34
CGC TGC ACG TGC TTC ACC TAC AAG GAC AAG
GAG TGT GTC TAC TAT TGC CAC CTG GAC ATC
96 ↓
ATT TGG ATC AAC ACT CCC GA It is as shown in FIG. 2 that this DNA sequence is also different from the known sequences and is novel.

The DNA sequence corresponding to mature proteins [corresponding to Nos. 34 to 96 in formulas (1) and (3)] are also different from the known endothelin DNA sequences, and hence the DNA sequences of the present invention are novel.

Human endothelin-3 precursor comprises the following amino acid sequence represented by the formula (4), which differs from the amino acid sequence of rat endothelin-3 precursor as shown in FIG. 2 and which is novel.

```
 1   2   3   4   5   6   7   8   9   10                (4)
Glu Gly Ala Pro Glu His His Arg Ser Arg 11  12  13  14  15  16  17  18  19  20
Arg Cys Thr Cys Phe Thr Tyr Lys Asp Lys 21  22  23  24  25  26  27  28  29  30
Glu Cys Val Tyr Tyr Cys His Leu Asp Ile 31  32  33  34  35  36  37
Ile Trp Ile Asn Thr Pro Glu
```

As the DNA sequences of the present invention coding for the endothelin-2 mature peptide (endothelin-2), any DNA sequence may be used as long as a DNA sequence contains a nucleotide sequence coding for the amino acid sequence [Nos. 12 to 32 in formula (2)]of the endothelin-2 mature peptide. For example, a DNA sequence containing the nucleotide sequence represented by formula (1) or a portion thereof is preferably used.

The nucleotide sequence represented by formula (1) is the endothelin-2 DNA sequence obtained in the present invention. The endothelin-2 amino acid sequence depicted in formula (2') corresponds to the nucleotide sequence represented by Nos. 34 to 96 in formula (1).

In the present invention, for example, an expression vector having the DNA sequence containing the nucleotide sequence coding for mature endothelin-2 can be prepared by the following process:

(a) Messenger RNA (mRNA) is isolated from endothelin-2 -producing cells.

(b) Single stranded complementary DNA (cDNA) is synthesized from the mRNA, followed by synthesis of double stranded DNA.

(c) The complementary DNA is introduced in a cloning vector such as a phage or a plasmid.

(d) Host cells are transformed with the recombinant phage or plasmid thus obtained.

(e) After cultivation of the transformants thus obtained, plasmids or phages containing the desired DNA are isolated from the transformants by an appropriate method such as hybridization with a DNA probe coding for a portion of endothelin-2 or immunoassay using an anti- endothelin-2 antibody.

(f) The desired cloned DNA sequence is cut out from the recombinant DNA.

(g) The cloned DNA sequence or a portion thereof is ligated downstream from a promoter in the expression vector.

The mRNA coding for endothelin-2 can be obtained from various endothelin-producing cells such as endothelial cells of human aortas and human placentas.

Methods for preparing the mRNA from the endothelin-2 -producing cells include the guanidine thiocyanate method J. M. Chirgwin et al., *Biochemistry* 18, 5294 (1979)] and the like.

Using the mRNA thus obtained as a template, cDNA is synthesized by use of reverse transcriptase, for example, in accordance with the method of H. Okayama et al. [*Molecular and Cellular Biology* 2, 161 (1979); *ibid.* 3, 280 (1983)]. The cDNA thus obtained is introduced into the plasmid.

The plasmids into which the cDNA may be introduced include, for example, pBR322 [*Gene* 2, 95 (1977)], pBR325 [*Gene* 4, 121 (1978)], pUC12 [*Gene* 19, 259 (1982)] and pUC13 [*Gene* 19, 259 (1982)], each derived from *Escherichia coli*, and pUB110 derived from *Bacillus subtilis* [*Biochemical and Biophysical Research Communication* 112, 678 (1983)]. However, any other plasmid can be used as long as it is replicable and growable in the host cell. Examples of the phage vectors into which the cDNA may be introduced include λgtll [R. Young and R. Davis, *Proc. Natl. Acad. Sci. U.S.A.* 80, 1194 (1983)]. However, any other phage vector can be used as long as it is growable in the host cell.

Methods for introducing the cDNA into the plasmid include, for example, the method described in T. Maniatis et al., *Molecular Cloning*, Cold Spring Harbor Laboratory, p.239 (1982). Methods for introducing the cDNA in the phage vector include, for example, the method of T. V. Hyunh et al. [*DNA Cloning, A Practical Approach* 1, 49 (1985)].

The plasmid thus obtained is introduced into an appropriate host cell such as Escherichia and Bacillus.

Examples of Escherichia described above include *Escherichia coli* K12DH1 [*Proc. Natl. Acad. Sci. U.S.A.* 60, 160 (1968)], M103 [*Nucleic Acids Research* 9, 309 (1981)], JA221 [*Journal of Molecular Biology* 120, 517 (1978)] HB101 [*Journal of Molecular Biology* 41, 459 (1969)] and C600 [*Genetics* 39, 440 (1954)].

Examples of Bacillus described above include *Bacillus subtilis* MI114 [*Gene* 24, 255 (1983)] and 207-21 [*Journal of Biochemistry* 95, 87 (1984)].

Methods for transforming the host cell with the plasmid include, for example, the calcium chloride method or the calcium chloride/rubidium chloride method described in T. Maniatis et al., *Molecular Cloning*, Cold Spring Harbor Laboratory, p.249 (1982).

When a phage vector is used, for example, the phage vector can be transduced into multiplied *Escherichia coli*, using the in vitro packaging method.

Human cDNA libraries containing endothelin-2 cDNA can be obtained by numerous techniques well known in the art including purchasing them from the market, though obtainable by the methods described above. For example, a cDNA library from human placentas is available from Clontech Laboratories, Inc., U.S.A.

Methods for cloning an endothelin-2 DNA from the human DNA library include, for example, the plaque hybridization method using oligonucleotides chemically synthesized on the basis of phage vector λcharon 4A and the amino acid sequence of endothelin-2 as a probe [T. Maniatis et al., *Molecular Cloning*, Cold Spring Harbor Laboratory, (1982)]. The endothelin-2 DNA thus cloned is subcloned in, for example, pBR322, pUC12, pUC13, pUC19, pUC118 and pUC119 to obtain the endothelin-2 DNA, if necessary.

The nucleotide sequence of the DNA sequence thus obtained is determined by, for example, the Maxam-Gilbert method [A. M. Maxam and W. Gilbert, *Proc. Natl. Acad. Sci. U.S.A.* 74, 560 (1977)] or the dideoxy method [J. Messing et al., *Nucleic Acids Research* 9, 309 (1981)], and the existence of the endothelin-2 DNA is confirmed in comparison with the known amino acid sequence.

As described above, the DNA sequence [endothelin-2 DNA, represented by formula (1)] coding for endothelin-2 is obtained.

FIG. 1 shows the restriction enzyme fragment maps of the DNA sequence containing the DNA segment coding for endothelin-2 obtained in Example 2 described below and of the DNA sequence containing the human endothelin-3 DNA obtained in Example 3 described below. FIG. 2 shows the nucleotide sequences of the DNA sequences as determined by the dideoxy method, and FIG. 3 shows the amino acid sequences ascertained from the nucleotide sequences.

The DNA sequence coding for endothelin-2 cloned as described above can be used as it is, or after digestion with a restriction enzyme if desired, depending on the intended use.

A region intended to be expressed is cut out from the cloned DNA and ligated downstream from the promoter in a vehicle (vector) suitable for expression, whereby the expression vector can be obtained.

The DNA sequence has ATG as a translation initiating codon at the 5'-terminus thereof and may have TAA, TGA or TAG as a translation terminating codon at the 3'-terminus. The translation initiating codon and translation terminating codon may be added by use of an appropriate synthetic DNA adaptor. A promoter is further ligated in the upstream thereof for the purpose of expressing the DNA sequence.

Examples of the vectors include the above plasmids derived from *Escherichia coli* such as pBR322, pBR325, pUC12, and pUC13, the plasmids derived from *Bacillus subtilis* such as pUB110, pTP5 and pC194, plasmids derived from yeast such as pSH19 and pSH15, bacteriophage such as λphage, and animal viruses such as retroviruses and vaccinia viruses.

As the promoter used in the present invention, any promoter is appropriate as long as the promoter is suitable for expression in the host cell selected for the gene expression.

When the host cell used for transformation is Escherichia, it is preferable that a trp promoter, a lac promoter, a recA promoter, a λPL promoter, a lpp promoter, etc. are used. When the host cell is Bacillus, it is preferable that a PH05 promoter, a PGK promoter, a GAP promoter, an ADH promoter, etc. are used. In particular, it is preferable that the host cell is Escherichia and the promoter is the trp promoter or the λPL promoter.

When the host cell is an animal cell, a SV-40 derived promoter, a retrovirus promoter, a metallothionein promoter, a heat shock promoter, etc. are each usable.

An enhancer, a certain DNA sequence important for promoter's activity in a cell, is also effectively used for expression.

Using a vector containing the DNA sequence coding for the endothelin-2 mature peptide (endothelin-2) thus constructed, transformants are prepared.

The host cells include, for example, Escherichia, Bacillus, yeast and animal cells.

As examples of the above Escherichia and Bacillus, strains similar to those described above can be mentioned.

Examples of the above yeast include *Saccharomyces cerevisiae* AH22, AH22R-, NA87-11A and DKD-5D.

Examples of the animal cells include monkey cell COS-7, Vero, Chinese hamster cell (CHO), mouse L cell and human FL cell.

The transformation of the above Escherichia is carried out according to, for example, the method described in *Proc. Natl. Acad. Sci. U.S.A.* 69, 2110 (1972) or *Gene* 17, 107 (1982).

The transformation of the above Bacillus is conducted according to, for example, the method described in *Molecular & General Genetics* 168, 111 (1979).

The transformation of the yeast is carried out according to, for example, the method described in *Proc. Natl. Acad. Sci. U.S.A.* 75, 1929 (1978).

The transformation of the animal cells is carried out according to, for example, the method described in *Virology* 52, 456 (1973).

Thus, there are obtained transformants transformed with an expression vector containing the DNA sequence coding for the endothelin-2 mature peptide (endothelin-2).

When bacterial transformants are cultured, a liquid medium is particularly suitable as a medium used for culture. Carbon sources, nitrogen sources, inorganic compounds and others necessary for growth of the transformant are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast extract, vitamins, growth promoting factors and so on may be further added thereto.

The pH of the medium is preferably about 5 to 8.

As the medium used for cultivation of Escherichia, there is preferred, for example, M9 medium containing glucose and Casamino Acids (Miller, *Journal of Experiments in Molecular Genetics* 431–433, Cold Spring Harbor Laboratory, New York, 1972). In order to make the promoter act efficiently, a drug such as 3-indolylacrylic acid may be added thereto if necessary.

When the host cell is Escherichia, the cultivation is usually carried out at about 15° to 43° C. for about 3 to 24 hours, with aeration or agitation if necessary.

When yeast transformants are cultured, there is used, for example, Burkholder minimum medium [K. L. Bostian et al., *Proc. Natl. Acad. Sci. U.S.A.* 77, 4505 (1980)] as the medium. The pH of the medium is preferably adjusted to about 5 to 8. The cultivation is usually carried out at about 20° to 35° C. for about 24 to 72 hours, with aeration or agitation if necessary.

When animal cell transformants are cultured, examples of the mediums include MEM medium containing about 5 to 20% fetal calf serum [*Science* 122, 501 (1952)], DMEM medium [*Virology* 8, 396 (1959)], RPMI1640 medium (*Journal of the American Medical Association* 199, 519 (1967)] and 199 medium [*Proceeding of the Society for the Biological Medicine* 73, 1 (1950). The pH is preferably about 6 to 8. The cultivation is usually carried out at about 30° to 40° C. for about 15 to 60 hours, with aeration or agitation if necessary.

The endothelin-2 mature peptide (endothelin-2) can be isolated and purified from the culture described above, for example, by the following method.

When the endothelin-2 mature peptide is to be extracted from the cultured cells, the cells are collected by methods known in the art after cultivation. Then, the collected cells are suspended in an appropriate buffer solution and disrupted by ultrasonic treatment, lysozyme and/or freeze-thawing. Thereafter, a crude extracted solution of the endothelin-2 mature peptide is obtained by centrifugation or filtration. The buffer solution may contain a protein denaturant such as urea or guanidine hydrochloride, or a surface-active agent such as Triton X-100.

When the endothelin-2 precursor protein or mature peptide is secreted in the culture solution, a supernatant is separated from the cells by methods known in the art after the conclusion of cultivation, and then collected.

The separation and purification of the endothelin-2 precursor protein or mature peptide contained in the culture supernatant or the extracted solution thus obtained can be performed by an appropriate combination of known separating and purifying methods. The known separating and purifying methods include methods utilizing solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse phase high performance liquid chromatography and methods utilizing a difference in isoelectric point such as isoelectro-focussing electrophoresis.

The activity of the endothelin-2 precursor protein or mature peptide thus formed can be measured by an enzyme immunoassay using a specific antibody. If the products have vasoconstrictive activity, this activity may also be measured as an index.

The methods for cloning endothelin-2 DNA and producing endothelin-2 protein, hereinbefore described, are similarly applicable for cloning of human endothelin-3 DNA and production of human endothelin-3 protein.

The cells, such as animal cells or *Escherichia coli*, transfected or transformed with the DNA sequence of the present invention allow large amounts of the endothelin-2 or endothelin-3 mature peptide to be produced. Hence, the production of these peptides can be advantageously achieved.

The endothelin-2 and endothelin-3 mature peptides prepared here not only can be utilized as hypotension therapeutic agents or local vasoconstrictors, but also give a clue to analysis of the mechanism of the vasoconstrictor reactions in vivo and to elucidation of antagonists to the vasoconstrictor factors, including the other endothelin peptides. Endothelin-2 has vasoconstrictor activity up to twice as high as the previously isolated endothelin peptides. These peptides have such effects as preventing various kinds of hemorrhage, for example, gastric or esophageal hemorrhage as vasoconstrictors, and may also be useful in curing various shock symptoms. The peptides can be administered orally, locally, intravenously or parenterally, preferably locally or intravenously. The dose is 0.001 $\mu$g to 100 $\mu$g/kg, preferably 0.01 $\mu$g to 10 $\mu$g/kg. The dose is preferably dependent on weight and preferably used in the form of a solution in 1 to 10 ml of a saline solution.

The peptides of the present invention can be formed into various preparations together with additional components, such as emulsions, hydrated mixtures, tablets, solutions, powders, granules, capsules and pills. Examples of the additional components include pharmaceutically acceptable vehicles, disintegrators, lubricants, binders, dispersants, plasticizers, fillers and carriers. As to the additional components, examples of the vehicles include lactose, glucose and white sugar; those of the disintegrators include starch, sodium alginate, agar powder and carboxymethyl cellulose calcium; those of the lubricants include magnesium stearate, talc and liquid paraffin; those of the binders include syrup, gelatin solution, ethanol and polyvinyl alcohol; those of the dispersants include methyl cellulose, ethyl cellulose and shellac; and those of the plasticizers include glycerin and starch.

When nucleotides, amino acids and so on are indicated by the abbreviations in this specification and drawings, the abbreviations adopted by IUPAC-IUB Commission on Biochemical Nomenclature or commonly used in the art are employed. For example, the following abbreviations are used. When amino acids are capable of existing as optical isomers, the L-forms are represented unless otherwise specified.

DNA : Deoxyribonucleic acid
cDNA : Complementary deoxyribonucleic acid
A : Adenine
T : Thymine
G : Guanine
C : Cytosine
RNA : Ribonucleic acid
mRNA : Messenger ribonucleic acid
dATP : Deoxyadenosine triphosphate
dTTP : Deoxythymidine triphosphate
dGTP : Deoxyguanosine triphosphate
dCTP : Deoxycytidine triphosphate
ATP : Adenosine triphosphate
EDTA : Ethylenediaminetetraacetic acid
SDS : Sodium dodecyl sulfate
Gly or G : Glycine
Ala or A : Alanine
Val or V : Valine
Leu or L : Leucine
Ile or I : Isoleucine
Ser or S : Serine
Thr or T : Threonine
Cys of C : Cysteine
Met or M : Methionine
Glu or E : Glutamic acid
Asp or D : Aspartic acid
Lys or K : Lysine
Arg or R : Arginine
His or H : Histidine
Phe or F : Phenylalanine
Tyr or Y : Tyrosine
Trp or W : Tryptophan
Pro of P : Proline
Asn or N : Asparagine
Gln or Q : Glutamine With respect to the endothelin-2 mature peptide and human endothelin-3 of the present invention, a portion of the amino acid sequence may be modified, namely there may be addition, elimination or substitution with other amino acids as long as the vasoconstrictor property is not lost.

The present invention will hereinafter be described in detail with the following Reference Example and Examples. It is understood that the Reference Example and Examples are not intended to limit the scope of the invention.

Transformant *Escherichia coli* XL-1/pghET20SG1 obtained in Example 2 and transformant *Escherichia coli* XL-1/pghET3E1 obtained in Example 3 are deposited in Fermentation Research Institute, Agency of Industrial Science and Technology, Ministry of International Trade and Industry, Japan (FRI) with the accession numbers FERM BP-2118 and FERM BP-2119, respectively, on Oct. 24, 1988.

REFERENCE EXAMPLE

(1) Assay of Vascular Smooth Muscle Constrictor Activity

Porcine right coronary artery spiral specimens (0.5×20 mm) with the intima denuded by rubbing with a small swab are suspended in 3 ml of Krebs-Ringer solution maintained at 37° C. and saturated with a mixed gas containing 5% carbon dioxide and 95% oxygen by volume. After setting the basal tension to 2 g, the isometric tension is measured with tension transducers.

(2) Assay of Cardiotonic Action

Instead of the porcine right coronary artery spiral specimens used in the assay described in the above item (1), suspended guinea pig right atrium specimens are used, and the tension and the heart rate per minute are measured according to the same procedure as described in (1).

EXAMPLE 1

Preparation of DNA Probe Coding for a Portion of Endothelin-1 [Porcine Endothelin (Human Endothelin I)]

The messenger RNA sequence expected from the amino acid sequence composed of the 7th to the 16th residues of endothelin-1, Met-Asp-Lys-Glu-Cys-Val-Tyr-Phe-Cys-His-Leu-Asp-Ile-Ile, was used to chemically synthesize a DNA probe having the following sequence.

$^{5'}$ATG GAC AAG GAG TGT GTC TAC TTC TGC CAT CTG GAC ATC ATC$^{3'}$

The 5'-terminus of this DNA probe was phosphorylated with [$\gamma$-$^{32}$p] ATP by using T4 polynucleotide kinase. The phosphorylated DNA probe was used for screening a genomic DNA library.

EXAMPLE 2

Isolation of Endothelin-2 Precursor Genomic DNA and Determination of Nucleotide Sequence Thereof

*Escherichia coli* Le392 was infected with the above human genomic DNA library (Clontech Laboratories, Inc.) and plated, whereby phage plaques were allowed to appear. According to the report of W. Benton and R. Davis [*Science* 196, 180–182 (1977)], a portion of plaque DNA was transferred to a nylon filter and hybridized with the DNA probe labeled with $^{32}$P in Example 1. The hybridization was carried out in the presence of 20% formamide at 42° C., and then the filter was washed in 0.2×SSC, 0.1% SDS at 20° C. Hybridization-positive clones were isolated. Then, a mature code region of λghET20, one of these clones, was cut out with SacI and subcloned in plasmid pUC118. By transforming *Escherichia coli* XL-1 with the resulting plasmid, transformant *Escherichia coli* XL-1/pghET20SG1 was obtained. There is shown in FIG. 1 the simplified restriction enzyme map of a human genomic DNA fragment contained in this plasmid. In the figure, the heavy bar (▧) shows a mature endothelin-2 code region.

This mature peptide code region and the nucleotide sequence in the vicinity thereof were determined by the method of Sanger [*Proc. Nat. Acad. Sci. U.S.A.* 74, 5463–5467 (1977)]. The nucleotide sequence and the amino acid sequence presumed therefrom are shown in FIG. 2. The region surrounded by (▭) shows the mature peptide portion. FIG. 3 shows, for comparison, the amino acid sequences of the mature peptides of endothelin-1, endothelin B and rat endothelin-3 which have previously been discovered, along with the amino acid sequence of the endothelin-2 mature peptide.

EXAMPLE 3

Isolation of Mature Human Endothelin-3 Code Region and Determination of Nucleotide Sequence Thereof Using methods similar to those in Example 2, hybridization-positive clones were isolated. Then, a mature code region of λghET3, one of these clones, was cut out with EcoRI and subcloned in plasmid pUC118. By transforming *Escherichia coli* XL-1 with the resulting plasmid, transformant *Escherichia coli* XL-1 with the resulting plasmid, transformant *Escherichia coli* XL-1/pghET3El was obtained. There is shown in FIG. 1 the simplified restriction enzyme map of a human genomic DNA fragment contained in this plasmid. In the figure, the heavy bar (▧) shows a mature human endothelin-3 code region.

This mature peptide code region and the nucleotide sequence in the vicinity thereof were determined by the method of Sanger [*Proc. Nat. Acad. Sci. U.S.A.* 74, 5463–5467 (1977)]. The nucleotide sequence and the amino acid sequence presumed therefrom are shown in FIG. 2. The region surrounded by a frame shows the endothelin-3 mature peptide portion.

EXAMPLE 4

(1) Synthesis of Endothelin-2

Human endothelin A-II was synthesized by a conventional method, using 0.7 g (0.5 m mol) of the commercially available Boc-Trp(CHO)-PAM resin (Applied Biosystems) and a peptide synthesizer (Applied Biosystems, Model 430A).

A condensation process was conducted as follows:

A Boc group on the resin was treated with 50% trifluoroacetic acid in methylene chloride to form a free terminal amino group, to which the following amino acids were condensed in turn according to the amino acid sequence of endothelin-2 from the C-terminus in the presence of dicyclohexyl carbodiimide (DCC);

Boc-Ile, Boc-Asp(OBzl), Boc-Leu, Boc-His(Tos), Boc-Cys(Acm), Boc-Tyr(Br-z), Boc-Val, Boc-Phe, Boc-Glu(OBzl), Boc-Lys(Cl-Z), Boc-Trp(CHO) and Boc-Ser(Bzl)

890 mg of 2.53 g of the protected endothelin-2 resin thus obtained was swelled with 1 ml of anisole and 1 ml of 1,2-ethanedithiole, and then treated with 10 ml of hydrogen fluoride at 0° C. for 60 minutes, followed by removal of excess hydrogen fluoride under reduced pressure. After washing with 5 ml of diethyl ether, the residue was extracted with trifluoroacetic acid and the resin was filtered off. After removal of trifluoroacetic acid by distillation under reduced pressure, the extract was dissolved in 50% aqueous acetic acid and applied on a dextran gel column (Sephadex G-50, 2×90 cm). Peak fractions eluted with the above solvent were collected and lyophilized, thereby obtaining 180 mg of white powder. In 4 ml of 50% aqueous acetic acid was dissolved 31 mg of the powder, and 19 mg of trifluoroacetate-mercury(II) was added thereto, followed by stirring at room temperature for 16 hours. The resulting mixture was diluted by addition of 100 ml of n-butanol, 50 ml of methanol and 50 ml of water, and sulfide gas was blown through it. Then, 5% NH₄OH was added thereto for adjustment to pH 8, and thereafter the mixture was subjected to air-oxidation for 6 hours. Acetic acid was further added thereto to give pH 3, followed by lyophilization. The lyophilized mixture was applied to a Sephadex G-50 column (2×90 cm) filled with 50% acetic acid, and the peak fractions were collected. The collected fractions were further fractionated by using HPLC [column: YMC (YMC Co. Ltd.), solvent: eluted by a linear gradient of 0.1% aqueous trifluoroacetic acid and acetonitrile containing 0.1% trifluoroacetic acid] to obtain 1.0 mg of the desired product.

Synthesized endothelin-2 was eluted by HPLC at 41.4 minutes, in contrast with 40.2 minutes for endothelin-1.

Column conditions

Wakosil 5C18(Wako Chem. Ind. Ltd., Japan)(4.6×250 mm)

Eluent: A (0.1% aqueous trifluoroacetic acid) B (acetonitrile containing 0.1% trifluoroacetic acid)

Linear concentration gradient elution from A to B (50 minutes)

Flow rate: 1.0 ml/minutes ( Values of analysis of amino acids: Values of analysis (the number in the synthesized product)

| Asx 1.92 (2) | Ser 2.31 (3) | Glx 1.04 (1) |
| Cys 1.30 (1) | Val 1.16 (1) | Ile 1.35 (1) |
| Leu 1.85 (2) | Tyr 0.89 (1) | Phe 1.01 (1) |
| His 1.10 (1) | Lys 1.03 (1) | Trp (*) (2) |

* No data was obtained due to acid decomposition.

The combination of the disulfide bonds was 1-15 and 3-11 cysteine groups in mature endothelin-2.

Assay

The activity of endothelin-2 obtained in the above item (1) was assayed by the method of the Reference Example.

$ED_{50}$ (median effective dose: effective dose for 50% of tested animals) measured by the assay (1) using porcine coronary artery was $8 \times 10^{-10}$ to $10 \times 10^{-10}$ mol/l.

(3) Injection preparation

12 µg of endothelin-2 obtained in (1) was dissolved in a saline solution and then filtered by a Millipore filter, followed by lyophilization. An intravenous injection preparation was prepared by dissolving the lyophilized produced in a saline solution to a total volume of 5 ml for use. The following references, which are referred to for their disclosures at various points in this application, are incorporated herein by reference.

Proc. Natl. Acad. Sci. U.S.A., 79, 5485 (1982)
Proc. Natl. Acad. Sci. U.S.A., 81, 4577 (1984)
Am. J. Physiol., 248, C550 (1985)
J. Cell. Physiol., 132, 263 (1987)
J. Pharmac. Exp. Ther., 236, 339 (1985)
Circ. Res., 60, 422 (1987)
Japanese Unexamined Patent Publication No. 206997/1989
Japanese Patent Application Nos. 275613/1987, 313155/1987, 148158/1988, 274454/1988, 174935/1988, 188083/1988 and 223389/1988
Biochemistry, 18, 5294 (1979)
Molecular and Cellular Biology, 2, 161 (1979)
Molecular and Cellular Biology, 3, 280 (1983)
Gene, 2, 95 (1977)
Gene, 4, 121 (1978)
Gene, 19, 259 (1982)
Biochemical and Biophysical Research Communication, 112, 678 (1983)
Proc. Natl. Acad. Sci. U.S.A., 80, 1194 (1983)
Molecular cloning, Cold Spring Harbor Laboratory, p.239 (1982)
DNA Cloning, A practical Approach, 1, 49 (1985)
Proc. Natl. Acad. Sci. U.S.A., 60, 160 (1968)
Nucleic Acids Research, 9, 309 (1981)
Journal of Molecular Biology, 120, 517 (1978)
Journal of Molecular Biology, 41, 459 (1969)
Genetics, 39, 440 (1954)
Gene, 24, 255 (1983)
Journal of Biochemistry, 95, 87 (1984)
Gene, 10, 63 (1980)
Proc. Natl. Acad. Sci. U.S.A., 74, 560 (1977)
Nucleic Acids Research, 1, 1513 (1979)
Molecular Cloning, Cold Spring Harbor Laboratory (1982)
Proc. Natl. Acad. Sci. U.S.A., 69, 2110 (1972)
Nucleic Acids Research 9, 309 (1981)
Gene, 17, 107 (1982)
Molecular & General Genetics, 168, 111 (1979)
Proc. Natl. Acad. Sci. U.S.A., 75, 1929 (1978)
Virology, 52, 456 (1973)
Journal of Experiments in Molecular Genetics, 431-433, 1972
Proc. Natl. Acad. Sci. U.S.A., 77, 4505 (1980)
Science, 122, 501 (1952)
Virology, 8, 396 (1959)
Journal of the American Medical Association, 199, 519 (1967)
Proceeding of the Society for the Biological Medicine, 73, 1 (1950)
Proc. Natl. Acad. Sci. U.S.A., 74, 5463-5467 (1977)
Science, 196, 180-182 (1977)

What is claimed is:

1. A protein having an amino acid sequence comprising:
Cys Ser Cys Ser Ser Trp Leu Asp Lys Glu Cys Val Tyr Phe Cys His Leu Asp Ile Ile Trp.

2. A protein having an amino acid sequence comprising: His Ala Gln Gly Thr His Leu Arg Leu Arg Arg Cys Ser Cys Ser Ser Trp Leu Asp Lys Glu Cys val Tyr Phe Cys His Leu Asp Ile Ile Trp Val Asn Thr Pro Glu.

* * * * *